(12) United States Patent
Simpson, Jr.

(10) Patent No.: US 8,324,178 B2
(45) Date of Patent: Dec. 4, 2012

(54) METHOD OF TREATMENT USING ALPHA-1-ADRENERGIC AGONIST COMPOUNDS

(75) Inventor: Paul C. Simpson, Jr., San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 292 days.

(21) Appl. No.: 12/610,720

(22) Filed: Nov. 2, 2009

(65) Prior Publication Data
US 2010/0113377 A1    May 6, 2010

Related U.S. Application Data

(60) Provisional application No. 61/110,400, filed on Oct. 31, 2008.

(51) Int. Cl.
*A61K 31/704* (2006.01)
*A61K 31/70* (2006.01)
*A61K 31/18* (2006.01)
*A61P 9/00* (2006.01)

(52) U.S. Cl. ............ 514/34; 514/25; 514/601; 514/605; 536/6.4; 536/4.1

(58) Field of Classification Search ............. 514/34, 514/25, 601, 605, 6.4, 4.1; 536/6.4, 4.1
See application file for complete search history.

(56) References Cited

U.S. PATENT DOCUMENTS

| | | | |
|---|---|---|---|
| 4,634,705 A | 1/1987 | DeBernardis et al. | |
| 5,610,174 A | 3/1997 | Craig et al. | |
| 5,620,993 A | 4/1997 | Patane et al. | |
| 6,323,231 B1 | 11/2001 | Brioni et al. | |
| 2001/0039255 A1 | 11/2001 | Brioni et al. | |

OTHER PUBLICATIONS

Aries et al., "Essential role of GATA-4 in cell survival and drug-induced cardiotoxicity", *PNAS*, 101(18):6975-6980 (2004).
Chan, Trevor, "Alpha1A-Adrenergic Receptor Agonist Therapy Activated Survival Signaling in Cardiac Myocytes and Prevents Doxorubicin-Induced Cardiomyopathy", Poster Abstract from Sarnoff Cardiovascular Research Foundation, Proceedungs of the 28th Annual Scientific Meeting, Georgetown University Conference Center, Washington, DC, May 1-4, 2008.
Gan et al., "Inhibition of Phenylephrine-Induced Cardiomyocyte Hypertrophy by Activation of Multiple Adenosine Receptor Subtypes", *The Journal of Pharmacology and Experimental Therapeutics*, 312:27-34 (2005).
Graham et al., "$\alpha_1$-Adrenergic Receptor Subtypes: Molecular Structure, Function and Signaling", *Circulation Research*, 78:737-749 (1996).
Hosoda et al., "Two $\alpha_1$-Adrenergic Receptor Subtypes Regulating the Vasopressor Response have Differential Roles in Blood Pressure Regulation", *Molecular Pharmacology*, 67:912-922 (2006).
Huang et al., "An $\alpha$1A-Adrenergic-Extracellular Signal-Regulated Kinase Survival Signaling Pathway in Cardiac Myocytes", *Circulation*, 115:763-772 (2007).
Knepper et al., "A-61603, a Potent $\alpha$1-Adrenergic Receptor Agonist, Selective for the alpha 1A Receptor Subtype", *The Journal of Pharmacology and Environmental Therapeutics*, 274:97-103 (1995).
O'Connell et al., "$\alpha_1$-Adrenergic Receptors Prevent a Maladaptive Cardiac Response to Pressure Overload", *J.Clin. Invest.*, 116:1005-1015 (2006).
Rokosh et al., "$\alpha_1$-Adrenergic Receptor Subtype mRNAs are Differentually Regulated by $\alpha$1-Adrenergic and other Hypertrophic Stimuli in Cardiac Myocytes in Culture and In Vivo", *The Journal of Biological Chemistry*, 271(10):5839-5843 (1996).
Rokosh et al., "Knockout of the $\alpha$1A/C-Adrenergic Receptor Subtype: The $\alpha$1A/C is Expressed in Resistance Arteries and is Required to Maintain Arterial Blood Pressure", *PNAS*, 99(14):9474-9479 (2002).
Rorabaugh et al., "$\alpha_{1A}$-but not $\alpha_{1B}$- Adrenergic Receptors Precondition the Ischemic Heart by a Staurosporine-Sensitive, Chelerythrine-Insensitive Mechanism", *Cardiovascular Research*, 65:436-445 (2005).
Shibata et al., "$\alpha_1$-Adrenergic Receptor Subtyoes Differentually Control the Cell Cycle of Transfected CHO Cells through a cAMP-Dependent Mechanism Involving p27$^{kip1}$", *The Journal of Biological Chemistry*, 278(1):672-678 (2003).
Woodcock et al., "Cardiac $\alpha_1$-Adrenergic Drive in Pathological Remodelling", *Cardiovasular Research*, 77:452-462 (2008).

*Primary Examiner* — Shaojia Anna Jiang
*Assistant Examiner* — Michael C Henry
(74) *Attorney, Agent, or Firm* — Kilpatrick Townsend & Stockton LLP

(57) ABSTRACT

Methods for treating or preventing cardiomyopathy in a subject by administering an $\alpha$1 adrenergic receptor agonist, wherein the treatment does not result in increased blood pressure are provided.

20 Claims, No Drawings

METHOD OF TREATMENT USING ALPHA-1-ADRENERGIC AGONIST COMPOUNDS

CROSS-REFERENCE TO RELATED APPLICATIONS

This application claims the benefit of U.S. Provisional Application No. 61/110,400, filed Oct. 31, 2008, incorporated herein by reference in its entirety.

STATEMENT REGARDING GOVERNMENT INTEREST

This work was supported in part by National Institute of Health Grant number HL31113 and the Department of Veterans Affairs Research Service. Accordingly the United States government has certain rights in this invention.

TECHNICAL FIELD

The subject matter described herein relates to a method of treating cardiomyopathy in a patient undergoing doxorubicin treatment, using an alpha-1-adrenergic agonist compound.

BACKGROUND

Anthracyclines are widely accepted as some of the most effective anti-cancer drugs (Weiss (1992), Semin. Oncol. 19:670-686). Nevertheless, clinical use of the anthracyclines doxorubicin (Dox) and daunorubicin (DNR) have proven to be hampered by side effects such as the development of resistance in tumor cells or toxicity in healthy tissues, most notably chronic cardiomyopathy and congestive heart failure (CHF). To avoid the latter, the maximum recommended cumulative dosages of DNR and Dox were tentatively set at 500 or 450 to 600 $mg/m^2$, respectively. Furthermore, there have been numerous attempts to identify novel anthracyclines that prove superior to DOX or DNR in terms of activity and/or cardiac tolerability. Unfortunately, few have reached the stage of clinical development and approval. Additional anthracyclines that have been approved for clinical use include epirubicin, idarubicin, pirarubicin, aclarubicin, and mitroxantrone (Minotti et al. (2004), Pharmacol. Rev. 56:185-229).

Doxorubicin is the most commonly used anthracycline in the treatment of hematological and solid malignancies. Doxorubicin-induced cardiomyopathy may be divided into acute, subacute, and late forms (Bristow et al. (1978), Cancer Treat. Rep. 62:873-879). The acute form is myocarditis/pericarditis syndrome that starts within 24 hours of the infusion and is not associated with poor long-term prognosis. Minor effects are picked up on the electrocardiogram (EKG) but in most cases resolve without any major problems. Subacute toxicity ensues weeks after Doxorubicin treatment but may be seen as late as 30 months. This form is associated with chronic changes and mortality may be as high as 60% (Goorin et al. (1981), Cancer, 47:2810-2816). Chronic toxicity may be evident as late as 4 to 20 years after the treatment with doxorubicin. It is accompanied by clinical heart failure and echocardiographic and pathologic changes.

Chronic cardiac changes that are due to doxorubicin appear to be irreversible, and the prognosis with doxorubicin-induced cardiomyopathy seems to be very poor without cardiac replacement therapy. Several agents have been employed for the attenuation of cardiomyopathic damaged induced by doxorubicin and include anti-oxidants, angiotensin converting enzyme inhibitors, and dexrazoxane. However, none have yet gained sufficient proof of efficacy to justify a routine use. It appears the only reliable medical treatment of this condition is its prevention (Hamed et al. (2006), Eur. Heart J. 27:1876-1883; Simsir et al. (2005), Ann. Thorac. Surg., 80:717-719).

The ultrastructural features of anthracycline-induced cardiomyopathy, characterized in patients' endomyocardial biopsies, include the loss of myofibrils, dilation of the sarcoplasmic reticulum, cytoplasmic vacuolization, swelling of mitochondria, and increased number of lysosomes. When severe, it leads to CHF.

Aries et al. (Proc. Natl. Acad. Sci. (2004), 101:6975-6980) showed that cardiotoxicity induced by Dox administration is correlated with a decrease in expression of the GATA-4 transcription factor, resulting in cardiomyocyte apoptosis. Aries et al. stated the results indicate that GATA-4 is an anti-apoptotic factor required for the adaptive stress response of the adult heart and suggests that use of $\alpha 1$-agonists in combination therapy with Dox may be beneficial to patients undergoing chemotherapy.

However, $\alpha 1_A$-AR agonists are well known to effect an increase in blood pressure. Indeed, $\alpha 1$-AR agonists, such as phenylephrine and methoxamine, are marketed as drugs to treat hypotension. Thus, while administration of alpha1-agonists to patients receiving Dox treatment may reduce or prevent cardiotoxicity, such treatment may result in a detrimental increase of blood pressure in the patient.

It has been surprisingly discovered that the compound N-[5-(4,5-Dihydro-1H-imidazol-2-yl)-2-hydroxy-5,6,7,8-tetrahydronaphthalen-1-yl]methanesulfonamide hydrobromide (known as A61603), when administered at an appropriate dose to a mammal undergoing Dox treatment, can provide beneficial reduction in cardiotoxicity without increasing blood pressure.

BRIEF SUMMARY

The following aspects and embodiments thereof described and illustrated below are meant to be exemplary and illustrative, not limiting in scope. Other limitations of the related art will become apparent to those of skill in the art upon a reading of the specification.

In one aspect, a method for treating or preventing cardiomyopathy, comprising administering A61603 to a subject undergoing treatment with an anthracycline a therapeutically effective dose of A61603, wherein the dose does not result in an increase in blood pressure, is provided.

In another aspect, a method for reducing the symptoms of cardiomyopathy, comprising administering A61603 to a subject undergoing treatment with an anthracycline a therapeutically effective dose of A61603, wherein the dose does not result in an increase in blood pressure is provided.

In one embodiment the anthracycline is selected from the group consisting of doxorubicin, daunorubicin, epirubicin, idarubucin, adriamycin and valrubicin.

In one embodiment, the dose of A61603 is between about 1 ng/kg/day and about 50 ng/kg/day, between about 5 ng/kg/day and about 40 ng/kg/day, between about 7 ng/kg/day and about 20 ng/kg/day, or between about 9 ng/kg/day and about 12 ng/kg/day. In another embodiment, the dose of A61603 is about 1 ng/kg/day, 2 ng/kg/day, 3 ng/kg/day, 4 ng/kg/day, 5 ng/kg/day, 6 ng/kg/day, 7 ng/kg/day, 8 ng/kg/day, 9 ng/kg/day, 10 ng/kg/day, 11 ng/kg/day, 12 ng/kg/day, 13 ng/kg/day, 14 ng/kg/day, 15 ng/kg/day, 16 ng/kg/day, 17 ng/kg/day, 18 ng/kg/day, 19 ng/kg/day, 20 ng/kg/day, 25 ng/kg/day, 30 ng/kg/day, 35 ng/kg/day, 40 ng/kg/day or 50 ng/kg/day.

In one embodiment, the dose of A61603 is co-administered with the anthracycline to the subject. In another embodiment, the dose of A61603 and the the anthracycline are administered to the subject on the same day.

In one embodiment, the dose of A61603 is administered to the subject after administration of the anthracycline. In another embodiment, the dose of A61603 is administered for 1, 2, 3, 4, 5, 6, 7, 8 or more consecutive days following the anthracycline administration. In yet another embodiment, the dose of A61603 is administered daily for a period of at least 1, 2, 3, 4, 5, 6, or 7 or more days.

In one embodiment, the dose of A61603 is administered to the subject prior to administration of the anthracycline. In another embodiment, the dose of A61603 is administered to the subject 1 or 2 days prior to administration of the anthracycline. In yet another embodiment, the dose of A61603 is administered at least 1, 2, 3, 4, 5, 6 hours prior to administration of the anthracycline.

In one embodiment, the dose A61603 is administered to the subject by a route selected from the group consisting of intravenous, intraanerial, buccal, sublingual, oral, peroral or transdermal, parenterally, orally, transdermally or nasally.

In one aspect, a method for treating or preventing anthracycline-induced cytotoxicity in a plurality of mammalian cardiac cells (myocytes) in a subject undergoing anthracycline treatment, without increasing the blood pressure of the subject is provided, comprising administering to the subject a therapeutically effective dose of A61603.

In one embodiment the anthracycline is selected from the group consisting of doxorubicin, daunorubicin, epirubicin, idarubicin, adriamycin and valrubicin.

In one embodiment, the method prevents a decrease in fractional shortening in the subject by more than 5%, 8%, 10%, 12%, 15% or 20% as compared to fractional shortening in a subject undergoing anthracycline treatment but not administered A61603.

In one embodiment, the method prevents an increase in the amount of creatine kinase or troponin in the serum of the subject by more than 2-fold, 4-fold, or 5-fold as compared to the amount of creatine kinase or troponin in the serum of the subject undergoing anthracycline treatment but not administered A61603.

In one embodiment, the method prevents an increase in the percentage of cardiac fibrosis area by more than 4%, 6%, 8%, 10% or 12% in the heart of the subject undergoing the anthracycline treatment but not administered A61603.

In addition to the exemplary aspects and embodiments described above, further aspects and embodiments will become apparent by reference by study of the following descriptions.

DETAILED DESCRIPTION

I. Definitions

As used herein, the terms "treatment," "treating" and the like generally mean obtaining a desired pharmacological and/or physiological effect by administering a therapeutic substance effective to reduce the symptoms of the condition and/or lessen the severity of the condition. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: preventing the disease from occurring in a subject which may be predisposed to the disease but has not yet been diagnosed as having it; inhibiting the disease. i.e., arresting its development; or relieving the disease, i.e., causing regression of the disease. More specifically, "treatment" may mean providing a therapeutically detectable and beneficial effect on a patient suffering from cardiomyopathy.

"Blood Pressure" is the pressure of the blood against the walls of the arteries when the heart beats (systolic pressure) and when the heart is at rest (diastolic pressure).

The term "effective amount," "amount effective," or "therapeutically effective amount," when referring to the amount of the A61603 or pharmaceutical . . . compound of the invention or pharmacologically active agent, is defined as that amount, or dose, of the compound or pharmacologically active agent that is sufficient for therapeutic efficacy (e.g., an amount sufficient to prevent or treat cardiomyopathy, reduce apoptosis in myocytes in vivo or in vitro, reduce fractional shortening, etc.).

As used herein, "pharmaceutically acceptable" means, for example, a carrier, diluent or excipient that is compatible with the other ingredients of the formulation and generally safe for administration to a recipient thereof or that does not cause an undesired adverse physical reaction upon administration.

The compound of the invention can be administered alone or as admixtures with conventional excipients, for example, pharmaceutically, or physiologically, acceptable organic, or inorganic carrier substances suitable for enteral or parenteral application which do not deleteriously react with the compound employed in the method. Suitable pharmaceutically acceptable carriers include water, salt solutions (such as Ringer's solution), alcohols, oils, gelatins and carbohydrates such as lactose, amylase or starch, fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances which do not deleteriously react with the compounds employed in the methods of the invention. The preparations can also be combined, when desired, with other active substances to reduce metabolic degradation.

As used herein, "subject" has its usual meaning and includes primates (e.g.; humans and nonhumans primates), experimental animals (e.g.; rodents such as mice and rats), farm animals (such as cows, hogs, sheep and horses), and domestic animals (such as dogs and cats).

As used herein "associated with" simply means both circumstances exist and should not be interpreted as meaning one necessarily is causally linked to the other.

II. Cardiomyopathy

Cardiomyopathy is a disease of the heart muscle. This form of heart disease is often distinctive, both in general symptoms and in patterns of blood flow, to allow a diagnosis to be made. Increasing recognition of this disease, along with improved diagnostic techniques, has shown that cardiomyopathy is the major cause of heart failure, which has high morbidity and mortality. In some areas of the world it may account for as many as 30 percent of all deaths due to heart disease.

Cardiomyopathy can result from a variety of structural or functional abnormalities of the ventricular myocardium. There are three clinical classifications of cardiomyopathy: hypertrophic, restrictive, and dilated congestive. Dilated congestive cardiomyopathy is a disorder of myocardial function where impaired systolic function and ventricular dilation occur, classified as ischemic or non-ischemic (toxic, genetic, idiopathic, etc). Restrictive cardiomyopathy is a rare form that occurs as a consequence of the ventricular walls becoming rigid so that the chambers are unable to fill adequately, caused for example by infiltration with amyloid or some other foreign material. Hypertrophic cardiomyopathy is characterized by ventricular hypertrophy and may be congenital or acquired, commonly caused by hypertension. The prognosis for all three types of disease is guarded at best and often poor. Treatment of cardiomyopathy involves beta-blockers, angiotensin converting enzyme inhibitors, use of anti-coagulants, and cardiac transplantation.

Cardiomyopathy, usually the dilated type, is well-known to result from the cardiotoxicity of doxorubicin in patients who receive a cumulative dose of more than about 500 mg/m$^2$. Although several mechanisms, such as free radical-dependent lipid peroxidation, mitochondrial impairment, and modification of cardiac calcium transport, have been reported to be the cause of the cardiotoxicity of anthracyclines, the precise mechanism of myocardial impairment remains unclear.

When cardiomyopathy is sufficiently advanced, it causes congestive heart failure, with physiological symptoms including breathlessness with exertion or even at rest, swelling of the legs, ankles and feet, bloating (distention) of the abdomen with fluid, fatigue, irregular heartbeats, and dizziness, lightheadedness and fainting.

III. The α1 Adrenergic Receptors

The α1 adrenergic receptors (α1-ARs) are important mediators of sympathetic nervous system responses, particularly those involved in cardiovascular homeostasis, such as arteriolar smooth muscle constriction and cardiac contraction. In addition, $\alpha_1$-ARs have more recently been implicated in the cardiac hypertrophy, cardio-protection, and in ischemic preconditioning. $\alpha_1$-ARs are activated by the catecholamines, norepinephrine and epinephrine.

The α1 adrenergic receptors are members of the superfamily of G protein-coupled receptors and mediate effects related to the regulation of cellular growth and function (Shibata et al. 2003, J. Biol. Chem. 278:672-678). $\alpha_1$-ARs consist of three subtypes: $\alpha_1$A-, $\alpha_1$B-, and $\alpha_1$D-ARs Graham et al., 1996. Circ. Res. 78:737-749). The three different $\alpha_1$-AR subtypes are expressed in different tissues and various cell types. As a result, studies on the physiological effects mediated by each of the $\alpha_1$-ARs in individual tissues are complicated by the co-existence of multiple $\alpha_1$-AR subtypes (Minneman et al. 1994, Mol. Pharmacol. 46:929-936; Minneman and Esbenshade, 1994. Annu. Rev. Pharmacol. Toxicol., 34:117-133; Weinberg et al, 1994; Biochem. Biophys Res. Commun. 201: 1296-1304; Esbenshade et al. 1995; Mol. Pharmacol. 47:977-985; Shibata et al. 1995; Mol. Pharmacol. 48:250-258).

IV. $\alpha_1$-Ars and Blood Pressure $\alpha_1$-ARs were discovered through their physiological effect to increase smooth muscle contraction (O'Connell et al. (2006), J. Clin. Invest. 116:1005-1015). $\alpha_1$-AR antagonist drugs are commonly used to treat disorders with increased smooth muscle contraction, such as hypertension and prostate enlargement with urinary symptoms. Examples of such drugs include doxazosin, terazosin, phenoxybenzamine and prazosin. These drugs, however, are not specific to a particular α1-AR subtype.

Accordingly, $\alpha_1$-AR agonists are generally considered to have therapeutic use in increasing blood pressure. Rokosh et al. (2002. Proc. Natl. Acad. Sci. 99:9474-9479) performed studies in which A61603 was administered to wild-type mice and to knock-out mice in which the first exon of $\alpha 1_A$-AR was replaced with a lacZ construct to produce a mouse deficient in $\alpha 1_A$-AR. Experiments showed that in the wild-type mice, infusion of A61603 resulted in increased mean arterial pressure (MAP) by 35 mm Hg, or 25% over basal, with an EC$_{50}$ 0.3 µg/kg, while in the knock-out mice, A61603 had no effect. These data indicated that the $\alpha 1_A$ receptor is a potent vasopressor in the normal mouse. From this study, the authors concluded that selective $\alpha 1_A$ receptor antagonists might be efficacious in treating hypertension.

V. A61603

A61603 has the chemical formula N-[5-(4,5-Dihydro-1 H-imidazol-2-yl)-2-hydroxy-5,6,7,8-tetrahydronaphthalen-1-yl]methanesulfonamide hydrobromide (see U.S. Pat. Nos. 4,634,705 and 6,323,231). A61603 is at least 35-fold more potent at $\alpha 1_A$ receptors than at $\alpha 1_B$ or alp sites (Knepper et al. (1995), J. Pharmacol. Exp. Ther., 274:97-103). A61603 is also a more potent $\alpha 1_A$ AR agonist than the non-selective α1 AR agonist phenylephrine.

VI. Method of Treatment

A method of treating or preventing doxorubicin-induced cardiomyopathy in a subject by administering A61603, wherein the administering does not cause hypertension or an increase in blood pressure, is provided. In the method disclosed herein, A61603, which activates the $\alpha 1_A$-adrenergic receptor in cardiac muscle, is administered to a mammal which has received or which is receiving doxorubicin treatments, to treat or prevent cardiomyopathy or cardiotoxicity.

In one embodiment, the dose of A61603 administered is one that does not result in an increase in blood pressure in the mammal, relative to the blood pressure prior to administration of the drug. Blood pressure is measured in millimeters of mercury (mm Hg). Blood pressure below about 120 over about 80 mmHg is desirable for adults. High blood pressure (or hypertension) in an adult is typically considered as a blood pressure greater than or equal to about 140 mm Hg systolic pressure or greater than or equal to about 90 mm Hg diastolic pressure. It will be appreciated that these values are merely typical, and that the actual blood pressure value will vary for a given individual, and will vary between individuals. Thus, in the present method, administration of A61603 with no increase in blood pressure is preferably with respect to the same individual's blood pressure measured, where possible, under the same conditions such as time of day and body position, before and after administration of the drug.

Therapeutically effective doses of A61603 for use in a mammal, which have no effect on blood pressure or which result in no significant increase in blood pressure, yet prevent the onset or progression of cardiomyopathy, are determined through standard methods in the art. An example of such a method is presented in Example 1 herein. Varying doses of A61603 are administered to a patient receiving doxorubicin treatment, followed by monitoring of blood pressure. Assays to determine whether or not A61603 is effective in preventing the onset of cardiomyopathy, or reducing its progression, are known to persons having ordinary skill in the art and include monitoring of fractional shortening, ejection fraction, end-diastolic volume and troponin levels (methods described in Bielecka-Dabrowa et al. 2008, Cardiology J. 278:1-5; Nellessen et al. 2006, Clin. Cardiol. 29:219-224). In one embodiment, no increase in blood pressure is observed when the blood pressure is measured 24 hours after treatment, in another embodiment no increase in blood pressure is observed when the blood pressure is measured 48 hours, 72 hours, 1 week or 1 month after treatment. In yet another embodiment, blood pressure, when measured 48 hours, 72 hours, 1 week, or 1 month, increases less than 10% or less than 15% after treatment with A61603.

In one embodiment, administration of the dose of A61603 at an amount which does not increase blood pressure prevents the onset or progression of cardiomyopathy in a patient undergoing doxorubicin treatment. Progression of cardiomyopathy may be monitored in part by measuring levels of serum biomarkers, such as creatine kinase, troponin, or brain natriuretic peptide (BNP).

Progression of cardiomyopathy may be assessed in part by measuring fractional shortening (FS) or ejection fraction (EF). FS is used to measure left ventricle performance by measuring the change in the diameter of the left ventricle between the contracted and relaxed state on M-mode tracings and calculating the ratio according to the formula: [(LV end-diastolic diameter−LV end-systolic diameter)/LV end-diastolic diameter)]×100. EF is calculated from left ventricular volumes determined by 2-dimensional echo, as [(LV end-diastolic volume−LV end-systolic volume)/LV end-diastolic volume)]×100-A decrease inFS or EF is indicative of heart damage due to cardiotoxicity. In one embodiment, a therapeutically effective amount of A61603 is administered to a subject undergoing doxorubicin treatment, wherein the A61603 prevents more than 10-20% reduction in the FS or EF as compared to a subject undergoing doxorubicin treatment but is not administered A61603. In another embodiment, administration of A61603 to a subject undergoing doxorubicin treatment prevents more than 5% reduction in the FS or EP as compared to a subject undergoing doxorubicin treatment but is not administered A61603.

In one embodiment, a therapeutically effective amount of A61603 is administered to a subject undergoing doxorubicin treatment, wherein the A61603 prevents more than 10-20% increase in the end-diastolic volume as compared to a subject undergoing doxorubicin treatment but is not administered A61603. In another embodiment, administration of A61603 to a subject undergoing doxorubicin treatment prevents more than 5% increase in the end-diastolic volume as compared to a subject undergoing doxorubicin treatment but is not administered A61603.

It is well known that creatine kinase (CK) or troponin are released from myocytes when myocyte necrosis occurs. Accordingly, measuring levels of CK or troponin in the serum may be done to assess the onset and progression of cardiomyopathy in a subject. Measuring serum CK levels is done using methods known to those of ordinary skill in the art, for example, by a coupled reaction of glucokinase and glucose-6-phosphate dehydrogenase using a diagnostic kit. In one embodiment, a therapeutically effective amount of A61603 is administered to a subject undergoing doxorubicin treatment, wherein the A61603 reduces the level of CK in the serum of the subject as compared to CK levels found in the serum of a subject undergoing doxorubicin treatment but is not administered A61603.

Another indicator of Dox-induced cardiomyopathy is increased cardiomyocyte apoptosis (Arola et al. (2000), Cancer Res. 60:1789-1702). Cardiomyopathy is also accompanied by an increase in fibrosis of the cardiac tissue. Fibrosis may be measured using Sirius Red staining, a method well-known to skilled artisans. In one embodiment, a therapeutically effective amount of A61603 is administered to a subject undergoing doxorubicin treatment, wherein the A61603 reduces the area of fibrosis in the heart as compared to a subject undergoing doxorubicin treatment but is not administered A61603.

For prevention, it will be appreciated that the A61603 can be administered to precondition the heart, for example, prior to an invasive cardiac procedure, such as a coronary intervention or a cardiac bypass.

The alpha-1-adrenergic agonist is administered parenterally, orally, transdermally, nasally, intravenously, intraanerially, sublingually, transdermally, or by any desired route of administration known in the pharmaceutical arts.

VII. Examples

The following examples are illustrative in nature and are in no way intended to be limiting.

EXAMPLE 1

Prevention of Cardiomypathy in Mice by Administering A61603

The alpha-1-adrenergic receptor agonist, A61603, was administered to 11 week-old wild type male C57BI6J mice using an osmotic minipump. Cardiomyopathy was induced with a single dose of doxorubicin (25 mg/kg) administered intraperitoneally. Blood pressure was measured by tail cuff, activated (phosphorylated) P-ERK by immunoblot, heart mRNA by RT-qPCR, fractional shortening (FS) by echocardiography (ECHO), myocyte necrosis by serum creatine kinase (CK), apoptosis by TUNEL stain, and fibrosis by Sirius red stain.

In a dose finding study, (0.01-100 μg/kg/day), A61603 at 10 ng/kg/day over 7 days had no effect on daily tail cuff blood pressure, as evidenced by the average blood pressure of the control, vehicle treated mice of 115±4 mmHg and the average blood pressure of the mice treated with A61603 of 119±4 mmHg. A61603 at higher doses increased blood pressure.

A61603 at the non-hypertensive dose of 10 ng/kg/day or vehicle was infused over 7 days after a single injection of doxorubicin. The table below shows that doxorubicin caused cardiomyopathy, with a reduced survival and fractional shortening, and increased necrosis, apoptosis, and fibrosis.

|  | Untreated | Doxorubicin + Vehicle | Doxorubicin + A61603 | P value (n) |
| --- | --- | --- | --- | --- |
| Survival 7 days (%) | 100 | 60 | 100 | <0.05 (13) |
| ECHO FS (%) | 66 ± 2 | 55 ± 3 | 67 ± 1 | <0.01 (8) |
| Serum CK (U/L) | 298 ± 3 | 1204 ± 98 | 571 ± 67 | <0.05 (5) |
| TUNEL-positive | 0.2 ± 0.01 | 1.3 ± 0.2 | 0.5 ± 0.1 | <0.05 (3) |
| Fibrosis area (%) | 24 ± 0.1 | 32 ± 1 | 25 ± 1 | <0.001 (5) |

Data are mean ± SE

In alpha-1A-subtype knock-out mice, doxorubicin caused increased apoptosis and mortality compared with wild-type mice, and A61603 had no beneficial result (data not shown), indicating specificity of A61603 for the alpha-1A adrenergic receptor.

In conclusion, a dose of an agonist selective for alpha-1A adrenergic receptor subtype can activate cardiac survival signaling (P-ERK), induce cardiac fetal genes, and prevent doxorubicin-induced cardiomyopathy, all without increasing blood pressure.

EXAMPLE 2

Prevention of Cardiomyopathy in Humans by Administering A61603

A patient in need of doxorubicin treatment is administered a dose of A61603 simultaneously with the doxorubicin, at a dose of A61603 which does not result in an increase in blood pressure. The patient first undergoes an A61603 dose-finding study. The dose-finding study is first performed in which the effects of a range of A61603 doses (0.01-100 µg/kg/day) is determined. The highest dose which does not result in an increase of blood pressure is used for co-administration with doxorubicin.

To delineate and assess the effectiveness of A61603 in preventing cardiomyopathy, the patient is monitored periodically throughout treatment with the A61603 and doxorubicin for changes in fractional shortening, ejection volume, and troponin levels in the serum, as described in more detail above.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope. All patents and publications cited above are hereby incorporated by reference.

It is claimed:

1. A method for treating cardiomyopathy, comprising administering to a subject undergoing treatment with an anthracycline a therapeutically effective dose of N-[5-(4,5-Dihydro-1 H-imidazol-2-yl)-2-hydroxy-5,6,7,8-tetrahydronaphthalen-1-yl]methanesulfonamide hydrobromide) (A61603), wherein the dose does not result in an increase in blood pressure.

2. The method of claim 1, wherein the anthracycline is selected from the group consisting of doxorubicin, daunorubicin, epirubicin, idarubicin, adriamycin and valrubicin.

3. The method of claim 1, wherein the dose is between about 5 ng/kg/day and 20 ng/kg/day.

4. The method of claim 3, wherein the dose is about 10 ng/kg/day.

5. The method of claim 1, wherein the A61603 is administered with the anthracycline.

6. The method of claim 1, wherein the A61603 is administered prior to the anthracycline administration.

7. The method of claim 1, wherein the A61603 is administered after the anthracycline administration.

8. The method of claim 1, wherein the A61603 is administered for at least 2 consecutive days after treatment with the anthracycline.

9. The method of claim 1, wherein the A61603 is administered by a route selected from the group consisting of intravenous, intraanerial, buccal, sublingual, oral, peroral, transdermal, parenteral, and nasal.

10. The method of claim 1, wherein the cardiomyopathy is dilated cardiomyopathy.

11. A method for reducing symptoms of cardiomyopathy, comprising administering to a subject undergoing treatment with an anthracycline a therapeutically effective dose of A61603, wherein the dose does not result in an increase in blood pressure.

12. The method of claim 11, wherein the A61603 is administered at a dose of between about 5 ng/kg/day and 20 ng/kg/day.

13. The method of claim 12, wherein the A61603 is administered at a dose of about 10 ng/kg/day.

14. The method of claim 11, wherein the A61603 is administered with the anthracycline.

15. The method of claim 11, wherein the A61603 is administered prior to the anthracycline administration.

16. The method of claim 11, wherein the A61603 is administered after the anthracycline administration.

17. The method of claim 11, wherein the A61603 is administered for at least 2 consecutive days after treatment with the anthracycline.

18. The method of claim 11, wherein the A61603 is administered by a route selected from the group consisting of intravenous, intraanerial, buccal, sublingual, oral, peroral, transdermal, parenteral, and nasal.

19. The method of claim 11, wherein the cardiomyopathy is dilated cardiomyopathy.

20. A method for treating or preventing anthracycline-induced cytotoxicity in a plurality of mammalian cardiac cells in a subject undergoing treatment with an anthracycline without increasing blood pressure comprising administering to the subject a therapeutically effective dose of A61603.

* * * * *